United States Patent [19]
Head et al.

[11] Patent Number: 5,849,770
[45] Date of Patent: Dec. 15, 1998

[54] TRI-SUBSTITUTED PHENYL DERIVATIVES USEFUL AS PDE IV INHIBITORS

[75] Inventors: John Clifford Head, Maidenhead; James Thomas Reuberson, Slough, both of United Kingdom

[73] Assignee: Celltech Therapeutics Ltd., Berkshire, United Kingdom

[21] Appl. No.: 769,465

[22] Filed: Dec. 20, 1996

[30] Foreign Application Priority Data

Dec. 21, 1995 [GB] United Kingdom .................. 9526245

[51] Int. Cl.⁶ .................... C07D 213/02; A61K 31/44
[52] U.S. Cl. .................... 514/357; 546/332; 546/336
[58] Field of Search .................. 546/336, 332; 514/357

[56] References Cited

U.S. PATENT DOCUMENTS

| | | | |
|---|---|---|---|
| 4,012,495 | 3/1977 | Schmiechen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |
| 5,693,659 | 12/1997 | Head et al. | 514/357 |
| 5,723,460 | 3/1998 | Warrellow et al. | 514/247 |

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 2 545 356 A1 | 11/1984 | France . |
| 250 1443 | 7/1975 | Germany . |
| 3-77872 | 4/1991 | Japan . |
| 3-77923 | 4/1991 | Japan . |
| 1588639 | 4/1984 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/09847 | 4/1995 | WIPO . |
| WO 95/09851 | 4/1995 | WIPO . |
| WO 95/09852 | 4/1995 | WIPO . |

(List continued on next page.)

OTHER PUBLICATIONS

Chatterjee, A. et al., "Total Synthesis of Ring–C Aromatic 18–Nor Steroid", *Tetrahedron*, 1980, 36, 2513–2519.

(List continued on next page.)

*Primary Examiner*—Zinna Northington Davis
*Attorney, Agent, or Firm*—Woodcock Washburn Kurtz Mackiewicz & Norris LLP

[57] ABSTRACT

Tri-substituted phenyl derivatives and pharmaceutical compositions containing them. In a preferred embodiment, the compounds have the general formula (2):

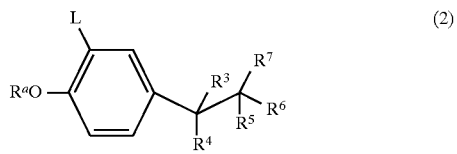

(2)

wherein L is preferably —OR; $R^a$ is preferably an optionally substituted alkyl group; R is preferably an optionally substituted cycloalkyl group; $R^3$ is preferably hydrogen; hydrogen, $R^4$ is preferably —$(CH_2)_tAr$, —$(CH_2)_t$—Ar—$(L^1)_n$—Ar' or —$(CH_2)_tArN(R^b)CX^1N(R^b)L^2(Alk)_mAr$; $R^5$ is preferably —$(CH_2)_tAr$, —$(CH_2)_t$—Ar—$(L^1)_n$—Ar' or —$(CH_2)_tArN(R^b)CX^1N(R^b)L^2(Alk)_mAr$; $R^6$ and $R^7$ are preferably hydrogen, $L^1$ and $L^2$ are preferably divalent linking groups; Ar is preferably a monocyclic or bicyclic aryl or heteroaryl group; and Ar' is preferably Ar or an Ar containing group. Compounds of the invention are potent and selective phosphodiesterase type IV inhibitors and are useful in the prophylaxis and treatment of various diseases, such as asthma, which are associated with an unwanted inflammatory response or muscular spasm.

28 Claims, No Drawings

FOREIGN PATENT DOCUMENTS

| | | |
|---|---|---|
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 96/14843 | 5/1996 | WIPO . |
| WO 97/09297 | 3/1997 | WIPO . |

OTHER PUBLICATIONS

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.,* 1961, 1863–1879.

Degani, I. et al., "Cationi etero–aromatici Nota VI –Sintesi di alcuni derivati del perclorato di tiacromilio", *Boll. Sci. Fac. Chim. Ind. Bologna,* 1966, 24(2–3), 75–91 (English Summary Only).

Geissler et al., "Biochemical and Biological Activity of a Novel Class of Tyrosine Protein Kinase Inhibitors", *J. Biol. Chem.,* 1990, 265(36), 22255–22261.

Griffin, R.W. et al., "1–Methyl–7–halo–2–naphthalenecarboxylic Acid Derivatives", *J. Organic Chem.,* 1964, 29(8), 2109–2116.

Gupta, A.S. et al., "Friedel–Crafts Condensation of Ethyl Allylmalonate with Anisole", *Tetrahedron,* 1967, 23, 2481–2490.

Hart et al., "Alkylation of Phenol with a Homoallylic Halide", *J. Am. Chem. Soc.,* 1963, 85, 3269–3273.

Johnson et al., "Identification of Retinoic Acid Receptor β Subtype Specific Agonists", *J. Med. Chem.,* 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis,* 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.,* 1964, 29, 1435–1438.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.,* 1994, 37, 1696–1703.

Beavo & Reifsnyder, "Primary Sequence of Cyclic Nucleotide Phosphodiesterase Isozymes and the Design of Selective Inhibitors" *TIPS,* 1990, 11, 150–155.

Buu–Hoi, N.P. et al., "Bromination of Some 1,2,2–Triarylethylenes" *J. of Organic Chemistry,* 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.,* 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.,* 1994, 12, 555–592.

Chemical Abstracts. Registry Handbook –Number Section. Printed Issues Columbus US *compounds with registry Nos. 95992–21–5; 95971–60–1; 90053–37–5; 82668–18–6; 80395–25–1; 49610–49–3 1996.

Daves, G.D. et al., "Pyrimidines. XIII. 2–and 6–Substituted 4–Pyrimidinecarboxylic Acids", *J. Of Hev. Chem.,* 1964, 1, 130–133.

Dietl, F. et al., "Chinone von Benzo–und Dibenzokronenethern", *Synthesis,* 1985, 626–631.

El–Wakil et al., "Study of the proton magnetic resonance of methoxytamoxifen towards ortho–substitiution", *Chem. Abstr.,* 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.,* 1990, 265(36), 22255–22261.

Hanks, S.K. et al., "The eukaryotic protein kinase superfamily: kinase (catalytic) domain structure and classification", *FASEB J.,* 1995, 9, 576–596.

Hirose et al., "Styrene Derivatives and Electrophotpgraphic Photoreceptor Containing Them", *Chem. Abstr.,* 1993, 118, 136183z.

Ishikura, M. et al., "An Efficient Synthesis of 3–Heteroarylpyridines via Diethyl–(3–pyridyl)–borane" *Synthesis,* 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling,* 1992, 4(2), 123–132.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)" *J. Heterocyclic Chem.,* 1979, 16, 711–715.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.,* 1980, 93, 95160j, 635.

Mitsunobu, O., "The Use of Diethyl Azodicarboxylate and Triphenylphosphine in Synthesis and Transformation of Natural Products" *Synthesis,* 1981, 1–28.

Newton, A.C., "Protein Kinase C: Structure, Function, Regulation", *J. Biol. Chem.,* 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS,* 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.,* 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.,* 1982, 613–621.

Pines, J., "Cyclins and cyclin–dependent kinases: take your partners", *TIBS,* 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sánchez, H.I. et al., "Formal Total Syntehsis of β–Pipitzol", *Tetrahedron*, 1985, 41(12), 2355–2359.

Schneider et al., "Catechol Estrogens of the 1,1,2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Thompson, W.J. and Gaudino, J., "A General Synthesis of 5–Arylnicotinates" *J. Org. Chem.*, 1984, 49, 5237–5243.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

Sakakibara, K. et al., "Preparation of N–pyridyl–4–(benzyloxy)benzamides as Cardiotonics", *Chem. Abstr.*, 1988, 108, No. 131583p.

Tsutsumi, K. et al., "Preparation of (Dialkoxyphosphinoymethyl)benzamides as Antihyperlipidemics", *Chem. Abstr.*, 1990, 113, No. 6599a.

Chemical Abstracts, "Hypoglycemic Pharmaceuticals Containing Manzammide Derivatives", *Chem. Abstr.*, 1983, 99(6), No. 43558Z.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2,3–, 3,4–et 2,4–, dimethoxybenzoylarylamines", *Bulletin DeLa Societa Chemique De France*, 1965, 848–858.

Green and Wuts, "Protective Groups in Organic Synthesis", John Wiley & Sons, New York, 1991.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Karlsson et al., "T–Lymphocyte and Inflammatory Cell Research in Asthma", Joller, G. et al. (eds.), Academic Press, 1993, 323–347.

Mathison et al., "Synthesis and Hypotensive Properties of Tetrahydroixoquinolines", *J. Med. Chem.*, 1973, 16(4), 332–336.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Vidal et al., "Electrophilic Amination: Preparation and Use of N–Boc–3–(4–cyanophenyl)oxaziridine, a New Reagent That Transfer a N–Boc Group to N–and C–Nucleophiles", *J. Org. Chem.*, 1993, 58, 4791–4793.

TRI-SUBSTITUTED PHENYL DERIVATIVES USEFUL AS PDE IV INHIBITORS

This invention relates to a novel series of triarylethanes, to processes for their preparation, to pharmaceutical compositions containing them, and to their use in medicine.

Many hormones and neurotransmitters modulate tissue function by elevating intra-cellular levels of adenosine 3',5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12:19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

In our International Patent Specification No. WO94/14742 we describe a series of triarylethanes which are potent inhibitors of the PDE IV isoenzyme at concentrations at which they have little or no inhibitory action on other PDE isoenzymes. The compounds are of use in medicine, especially in the prophylaxis and treatment of asthma. An enantioselective process for the preparation of these compounds is described in our International Patent Specification No. WO95/17386.

We have now found a particular series of triarylethanes which are potent and selective PDE IV inhibitors and which also have other advantageous pharmacological properties, including especially good oral availability and improved metabolic stability.

Thus according to one aspect of the invention, we provide a compound of formula (1)

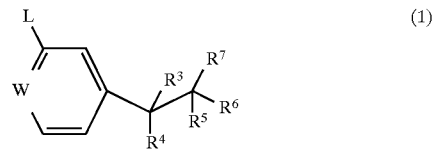

(1)

wherein
=W— is (1) =C(Y)— where Y is a halogen atom, or an alkyl or —$XR^a$ group where X is —O—, —$S(O)_p$— [where p is zero or an integer of value 1 or 2], or —$N(R^b)$— [where $R^b$ is a hydrogen atom or an optionally substituted alkyl group] and $R^a$ is a hydrogen atom or an optionally substituted alkyl group or, (2) =N—;

L is a —XR, [where R is an optionally substituted alkyl, alkenyl, cycloalkyl or cyloalkenyl group], —$C(R^{11})$=$C(R^1)(R^2)$ or [—$CH(R^{11})]_n CH(R^1)(R^2)$ group where $R^{11}$ is a hydrogen or a fluorine atom or a methyl group, and $R^1$ and $R^2$, which may be the same or different, is each a hydrogen or fluorine atom or an optionally substituted alkyl, alkenyl, alkynyl, alkoxy, alkylthio, —$CO_2R^8$, [where $R^8$ is a hydrogen atom or an optionally substituted alkyl, aralkyl, or aryl group], —$CONR^9R^{10}$ [where $R^9$ and $R^{10}$, which may be the same or different is each as defined for $R^8$], —$CSNR^9R^{10}$, —CN or —$NO_2$ group, or $R^1$ and $R^2$ together with the C atom to which they are attached are linked to form an optionally substituted cycloalkyl or cycloalkenyl group and n is zero or the integer 1;

$R^3$ is a hydrogen or a fluorine atom, an optionally substituted straight or branched alkyl group, or a hydroxyl group;

$R^4$ is a hydrogen atom or group —$(CH_2)_t Ar$ [where t is zero or an integer 1, 2 or 3 and Ar is a monocyclic or bicyclic aryl group, optionally containing one or more heteroatoms selected from oxygen, sulphur or nitrogen atoms] or a group —$(CH_2)_t$—Ar—$(L^1)_n$—Ar' [where $L^1$ is a divalent linking group n is zero or an integer 1 and Ar' is —Ar, —CO(Alk)$_m$Ar, [where Alk is an optionally substituted straight or branched $C_{1-6}$ alkylene, $C_{2-6}$ alkenylene or $C_{2-6}$ alkynylene chain optionally interrupted by one, two or three —O— or —S— atoms or —S(O)q— (where q is an integer 1 or 2) or —$N(R^b)$— groups and m is zero or an integer 1], —$SO_2$(Alk)$_n$Ar, —$SO_2NH(Alk)_m Ar$, —$SO_2N(Alk^1)(Alk)_m Ar$ [where $Alk^1$ is as defined for Alk] —$SO_2N[(Alk)_m Ar]_2$, —$CONH(Alk)_m Ar$, —$CON(Alk^1)(Alk)_m Ar$, —$CON[(Alk)_m Ar]_2$, —$N(Alk^1)SO_2(Alk)_m Ar$, —$NHSO_2(Alk)_m Ar$, —$N[SO_2(Alk)_m Ar]_2$, —$NHSO_2NH(Alk)_m Ar$, —$N(Alk^1)SO_2NH(Alk)_m Ar$, —$NHSO_2N(Alk^1)(Alk)_m Ar$, —$N(Alk^1)SO_2N(Alk^1)(Alk)_m Ar$, —$N(Alk^1)SO_2N[(Alk)_m Ar]_2$, —$N(Alk^1)SO_2N[(Alk)_m Ar]_2$, —$NHC(O)(Alk)_m Ar$, —$N(Alk^1)C(O)(Alk)_m Ar$, —$N[C(O)(Alk)_m Ar]_2$, —$NHC(O)NH(Alk)_m Ar$, —$N(Alk^1)C(O)NH(Alk)_m Ar$, —$NHC(O)N(Alk^1)(Alk)_m Ar$, —$N(Alk^1)C(O)N(Alk^1)(Alk)_m Ar$, —$NHC(O)O(Alk)_m Ar$, —$N(Alk^1)C(O)O(Alk)_m Ar$, —$C(S)NH(Alk)_m Ar$, —$C(S)N(Alk^1)(Alk)_m Ar$, —$C(S)N(Alk^1)(Alk)_m Ar$, —$C(S)N[(Alk)_m Ar]_2$, —$NHC(S)(Alk)_m Ar$, —$N(Alk^1)C(S)(Alk)_m Ar$, —$N[C(S)(Alk)_m Ar]_2$, —$NHC(S)NH(Alk)_m Ar$, —$N(Alk^1)C(S)NH(Alk)_m Ar$, —$NHC(S)N(Alk^1)(Alk)_m Ar$, —$N(Alk^1)C(S)N(Alk^1)(Alk)_m Ar$, —$SO_2(Alk)_m NHet$ [where —NHet is an optionally substituted $C_{5-7}$ heterocyclic amino group optionally containing one or more other —O— or —S— atoms or —$N(R^b)$—, —C(O)— or —C(S)— groups], —CO(Alk)$_m$NHet, —CS(Alk)$_m$NHet, —$NHSO_2(Alk)_m NHet$, —$NHC(O)(Alk)_m NHet$, —$NHC(S)(Alk)_m NHet$, —$SO_2NH((Alk)_m Het')$ [where Het' is an optionally substituted $C_{5-7}$monocyclic carbocyclic group optionally containing one or more —O— or —S— atoms or —$N(R^b)$— groups], —$CONH((Alk)_m Het')$, —$CSNH((Alk)_m Het')$, —$NHSO_2NH((Alk)_m Het')$, —$NHC(O)NH(Alk)_m(Het')$ or —$NHC(S)NH(Alk)_m(Het')$ group] or $R^4$ is a —$(CH_2)_t ArN(R^b)CX^1N(R^b)L^2(Alk)_m Ar$ group where X is an oxygen or sulphur atom and $L^2$ is a divalent linking group;

$R^5$ is a —$(CH_2)_t Ar$, —$(CH_2)_t$—Ar—$(L^1)_n$—Ar' or —$(CH_2)_t ArN(R^b)CX^1N(R^b)L^2(Alk)_m Ar$ group, provided that at least one of $R^4$ or $R^5$ is a —$(CH_2)_t ArN(R^b)CX^1N(R^b)L^2(Alk)_m Ar$ group;

$R^6$ is a hydrogen or a fluorine atom, or an optionally substituted alkyl group;

$R^7$ is a hydrogen or a fluorine atom, an optionally substituted straight or branched alkyl group or an $OR^c$ group where $R^c$ is a hydrogen atom or an optionally substituted alkyl or alkenyl group, or an alkoxyalkyl, alkanoyl, formyl, carboxamido or thiocarboxamido group; and the salts, solvates, hydrates, prodrugs and N-oxides thereof.

It will be appreciated that certain compounds of formula (1) may have one or more chiral centres, depending on the nature of the groups L, $R^1$, $R^2$, $R^3$, $R^4$, $R^5$, $R^6$ and $R^7$. Where one or more chiral centres is present, enantiomers or diastereomers may exist, and the invention is to be understood to extend to all such enantiomers, diastereomers and mixtures thereof, including racemates.

Compounds of formula (1) wherein L is a —C($R^{11}$)=C($R^1$)($R^2$) group may exist as geometric isomers depending on the nature of the groups $R^1$, $R^2$, and $R^{11}$ and the invention is to be understood to extend to all such isomers and mixtures thereof.

In the compounds of formula (1), when =W— is =C(Y)— and Y is a halogen atom Y may be for example a fluorine, chlorine, bromine or iodine atom.

When W in the compounds of formula (1) is a group =C(Y)— and Y is —$XR^a$, $R^a$ may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example —$CH_2F$, —$CH_2Cl$, —$CHF_2$, —$CHCl_2$, —$CF_3$ or —$CCl_3$ groups.

When =W— in the compounds of formula (1) is a group =C(Y)— where —Y is —N($R^b$), =W— may be a =C($NH_2$)—, =C($NHCH_3$)— or =C($NHC_2H_5$)— group.

In compounds of formula (1), X may be an oxygen or a sulphur atom, or a group —S(O)—, —S(O)$_2$—, —NH— or $C_{1-6}$ alkylamino, for example a $C_{1-3}$ alkylamino, e.g. methylamino [—N($CH_3$)—] or ethylamino [—N($C_2H_5$)—] group.

Alkyl groups represented by Y, R, $R^1$, $R^2$, or $R^b$ in the compounds of formula (1) include optionally substituted straight or branched C1–6 alkyl groups optionally interrupted by one or more X atoms or groups. Particular examples include $C_{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy or —$CO_2R^8$, —$CONR^9R^{10}$, —$CSNR^9R^{10}$ or —CN groups.

Alkenyl groups represented by R, $R^1$ or $R^2$ in the compounds of formula (1) include optionally substituted straight or branched $C_{2-6}$alkenyl groups optionally interrupted by one or more X atoms or groups. Particular examples include ethenyl, propen-1-yl and 2-methylpropen-1-yl groups. Optional substituents include those described above in relation to alkyl groups represented by the groups $R^1$ or $R^2$.

Alkynyl groups represented by $R^1$ or $R^2$ in compounds of formula (1) include optionally substituted straight or branched $C_{2-6}$alkynyl groups optionally interrupted by one or more X atoms or groups. Particular examples include ethynyl and propyn-1-yl groups. Optional substituents include those described above in relation to alkyl groups represented by the groups $R^1$ or $R^2$.

When $R^1$ or $R^2$ in compounds of formula (1) is an alkoxy or alkylthio group it may be for example an optionally substituted straight or branched $C_{1-6}$ alkoxy or $C_{1-6}$alkylthio group optionally interrupted by one or more X atoms or groups. Particular examples include $C_{1-3}$alkoxy, e.g. methoxy or ethoxy, or $C_{1-3}$alkylthio e.g. methylthio or ethylthio groups. Optional substituents include those described above in relation to alkyl groups represented by the groups $R^1$ or $R^2$.

When $R^1$ and $R^2$ together with the carbon atom to which they are attached in the compounds of formula (1) are linked to form a cycloalkyl or cycloalkenyl group, the group may be for example a $C_{3-8}$cycloalkyl group such as a cyclobutyl, cyclopentyl or cyclohexyl group or a $C_{3-8}$ cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

When R in the compounds of formula (1) is an optionally substituted cycloalkyl or cycloalkenyl group it may be for example a $C_{3-8}$cycloalkyl group such as a cyclobutyl, cyclopentyl or cyclohexyl group or a $C_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

When the group $R^7$ in compounds of formula (1) is an $OR^c$ group it may be for example a hydroxyl group; or a group —$OR^c$ where $R^c$ is an optionally substituted straight or branched $C_{1-6}$alkyl group, e.g. a $C_{1-3}$alkyl group such as a methyl or ethyl group, a $C_{2-6}$alkenyl group such as an ethenyl or 2-propen-1-yl group, a $C_{1-3}$alkoxy$C_{1-3}$alkyl group such as a methoxymethyl, ethoxymethyl or ethoxyethyl group, a $C_{1-6}$alkanoyl, e.g. $C_{1-3}$alkanoyl group such as an acetyl group, or a formyl [HC(O)—], carboxamido (CONR$^{12}$R$^{12a}$) or thiocarboxamido (CSNR$^{12}$R$^{12a}$) group, where $R^{12}$ and $R^{12a}$ in each instance may be the same or different and is each a hydrogen atom or an optionally substituted straight or branched $C_{1-6}$alkyl, e.g. $C_{1-3}$alkyl group such as methyl or ethyl group. Optional substituents which may be present on such $R^c$, $R^{12}$ or $R^{12a}$ groups include those described below in relation to the alkyl groups $R^6$ or $R^7$.

Alkyl groups represented by $R^3$, $R^6$ or $R^7$ in compounds of formula (1) include optionally substituted straight or branched $C^{1-6}$ alkyl groups, e.g. $C_{1-3}$ alkyl groups such as methyl, ethyl, n-propyl or i-propyl groups. Optional substituents which may be present on these groups include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups.

When the group $R^6$ in compounds of formula (1) is a halogen atom it may be for example a fluorine, chlorine, bromine or iodine atom.

When $R^1$ or $R^2$ is a —$CO_2R^8$, —$CONR^9R^{10}$ or $CSNR^9R^{10}$ group or these groups appear as substituents, the groups may be for example a —$CO_2H$, —$CONH_2$ or —$CSNH_2$ group or a group —$CO_2R^8$, —$CONR^9R^{10}$, —$CSNR^9R^{10}$, —$CONHR^{10}$, or —$CSNHR^{10}$ where $R^8$, $R^9$ and $R^{10}$ where present is a $C_{1-3}$alkyl group such as methyl or ethyl group, a $C_{6-12}$aryl group, for example an optionally substituted phenyl, or a 1- or 2- naphthyl group, or a $C_{6-12}$aryl $C_{1-3}$alkyl group such as an optionally substituted benzyl or phenethyl group. Optional substituents which may be present on these aryl groups include $R^{13}$ substituents discussed below in relation to the group Ar.

In the compounds of formula (1), the groups —(CH$_2$)$_r$Ar and —(CH$_2$)$_r$Ar(L$^1$)$_n$Ar' when present may be —Ar, —CH$_2$Ar, —(CH$_2$)$_2$Ar, —(CH$_2$)$_3$Ar—, —Ar—Ar', —Ar—L$^1$—Ar', —CH$_2$ArAr', —CH$_2$ArL$^1$Ar', —(CH$_2$)$_2$ArAr', —(CH$_2$)$_2$ArL$^1$Ar', —(CH$_2$)$_3$ArAr' or —(CH$_2$)$_3$ArL$^1$Ar' groups.

Monocyclic or bicyclic aryl groups represented by the group Ar or Ar' in compounds of formula (1) include for example C$_{6-12}$ optionally substituted aryl groups, for example optionally substituted phenyl, 1-or 2-naphthyl, indenyl or isoindenyl groups.

When the monocyclic or bicyclic aryl group Ar or Ar' contains one or more heteroatoms, Ar or Ar' may be for example a C$_{1-9}$ optionally substituted heteroaryl group containing for example one, two, three or four heteroatoms selected from oxygen, sulphur or nitrogen atoms. In general, Ar or Ar' heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten- membered heteroaryl groups containing one, two or more heteroatoms selected from oxygen, sulphur or nitrogen atoms.

Examples of heteroaryl groups represented by Ar or Ar' include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b] pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar or Ar' may be attached to the remainder of the molecule of formula (1) through any ring carbon or heteroatom as appropriate. Thus, for example, when the group Ar or Ar' is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar or Ar' is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8- isoquinolinyl group.

When in compounds of formula (1) the Ar or Ar' group is a nitrogen-containing heterocycle it may be possible to form quaternary salts, for example N-alkyl quaternary salts and the invention is to be understood to extend to such salts. Thus for example when the group Ar or Ar' is a pyridyl group, pyridinium salts may be formed, for example N-alkylpyridinium salts such as N-methylpyridinium.

The aryl or heteroaryl groups represented by Ar or Ar' in compounds of formula (1) may each optionally be substituted by one, two, three or more substituents [R$^{13}$]. The substituent R$^{13}$ may be selected from an atom or group R$^{14}$ or —Alk$^2$(R$^{14}$)$_m$ wherein R$^{14}$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^2$, —SO$_3$H, —SO$_2$Alk$^2$, —SO$_2$NH$_2$, —SO$_2$NHAlk$^2$, —SO$_2$N[Alk$^2$]$_2$, —CONH$_2$, —CONHAlk$^2$, CON[Alk$^2$]$_2$, —NHSO$_2$H, —NAlk$^2$SO$_2$H, —NHSO$_2$Alk$^2$, —NAlk$^2$SO$_2$Alk$^2$, —N[SO$_2$Alk$^2$]$_2$, —NHSO$_2$NH$_2$, —NAlk$^2$SO$_2$NH$_2$, —NHSO$_2$NHAlk$^2$, —NAlk$^2$SO$_2$NHAlk$^2$, —NHSO$_2$N[Alk$^2$]$_2$, —NAlk$^2$SO$_2$N[Alk$^2$]$_2$, —NHC(O)H, —NHC(O)Alk$^2$, —NAlk$^2$C(O)H, —NAlk$^2$C(O)Alk$^2$, —N[C(O)Alk$^2$]$_2$, —NHC(O)OH, —NHC(O)OAlk$^2$, —NAlk$^2$C(O)OH, —NAlk$^2$C(O)OAlk$^2$, —NHCONH$_2$, —NHCONHAlk$^2$, —NHCON[Alk$^2$]$_2$, —NAlk$^2$CON[Alk$^2$]$_2$, —NAlk$^2$CONH[Alk$^2$], —NAlk$^2$CONH$_2$, —C(S)H, —C(S)Alk$^2$, —CSNH$_2$, —CSNHAlk$^2$, —CSN[Alk$^2$]$_2$, —NHC(S)H, —NHCSAlk$^2$, —NAlk$^2$C(S)H, —NAlk$^2$C(S)Alk$^2$, —N[C(S)Alk$^2$]$_2$, —N[C(O)Alk$^2$]SO$_2$H, —NHCSNH$_2$, —NHCSNHAlk$^2$, —NHCSN[Alk$^2$]$_2$, —NAlk$^2$CSN[Alk$^2$]$_2$, —NAlk$^2$CSNHAlk$^2$, —NAlk$^2$CSNH$_2$, or —N[C(O)Alk$^2$] SO$_2$Alk$^2$ group, Alk$^2$ is a straight or branched C$_{1-6}$ alkylene, C$_{2-6}$alkenylene, or C$_{2-6}$alkynylene chain optionally interrupted by one, two, or three —O—, or —S— atoms or —S(O)p—, [where p is an integer 1 or 2] or —N(R$^8$)— groups; and m is zero or an integer 1, 2 or 3.

When in the group —Alk$^2$(R$^{14}$)$_m$ m is an integer 1, 2 or 3, it is to be understood that the substituent or substituents R$^{14}$ may be present on any suitable carbon atom in —Alk$^2$. Where more than one R$^{14}$ substituent is present these may be the same or different and may be present on the same or different carbon atom in Alk$^2$. Clearly, when m is zero and no substituent R$^{14}$ is present or when Alk$^2$ forms part of a group such as —SO$_2$Alk$^2$ the alkylene, alkenylene or alkynylene chain represented by Alk$^2$ becomes an alkyl, alkenyl or alkynyl group.

When R$^{14}$ is a substituted amino group it may be a group —NH[Alk$^2$(R$^{14a}$)$_m$] [where Alk$^2$ and m are as defined above and R$^{14a}$ is as defined above for R$^{14}$ but is not a substituted amino, a substituted hydroxyl or a substituted thiol group] or a group —N[Alk$^2$(R$^{14a}$)$_m$]$_2$ wherein each —Alk$^2$(R$^{14a}$)$_m$ group is the same or different.

When R$^{14}$ is a halogen atom it may be for example a fluorine, chlorine, bromine, or iodine atom.

When R$^{14}$ is a cycloalkoxy group it may be for example a C$_{5-7}$cycloalkoxy group such as a cyclopentyloxy or cyclohexyloxy group.

When R$^{14}$ is a substituted hydroxyl or substituted thiol group it may be a group —OAlk$^2$(R$^{14a}$)$_m$ or —SAlk$^2$(R$^{14a}$)$_m$ respectively, where Alk$^2$, R$^{14a}$ and m are as just defined.

Esterified carboxyl groups represented by the group R$^{14}$ include groups of formula —CO$_2$Alk$^3$ wherein Alk$^3$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^3$ group include R$^{13}$ substituents described above.

It will be appreciated that the group Ar or Ar' may be attached to the remainder of the molecule of formula (1) through either a ring carbon atom or heteroatom.

Particular examples of the chain Alk$^2$ when present include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^b$)— groups.

Particularly useful atoms or groups represented by R$^{13}$ include fluorine, chlorine, bromine or iodine atoms, or C$_{1-6}$alkyl, e.g. methyl or ethyl, C$_{1-6}$alkylamino, e.g. methylamino or ethylamino, C$_{1-6}$ hydroxyalkyl, e.g. hydroxymethyl or hydroxyethyl, C$_{1-6}$alkylthiol e.g. methylthiol or ethylthiol, C$_{1-6}$alkoxy, e.g. methoxy or ethoxy, C$_{5-7}$cycloalkoxy, e.g. cyclopentyloxy, haloC$_{1-6}$alkyl, e.g. trifluoromethyl, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, nitro, cyano, hydroxyl (—OH), formyl [HC(O)—], carboxyl (—CO$_2$H), —CO$_2$Alk$^3$ [where Alk$^3$ is as defined above], C$_{1-6}$ alkanoyl e.g. acetyl, thiol (—SH), thioC$_{1-6}$alkyl, e.g. thiomethyl or thioethyl, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, C$_{1-6}$alkanoylaminoC$_{1-6}$alkyl, e.g. acetylaminomethyl or C$_{1-6}$ alkoxycarbonylamino, e.g. methoxycarbonylamino, ethoxycarbonylamino or t-butoxycarbonylamino thiocarboxamido (—CSNH$_2$), C$_{1-6}$ alkylaminothiocarbonyl, e.g. methylaminothiocarbonyl or ethylaminothiocarbonyl, C$_{1-6}$dialkylaminothiocarbonyl, e.g. dimethylaminothiocarbonyl or diethylaminothiocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, aminothiocarbonylamino, C$_{1-6}$alkylaminothiocarbonylamino, e.g. methylaminothiocarbonylamino or ethylaminothiocarbonylamino, C$_{1-6}$ dialkylaminothiocarbonylamino, e.g. dimethylaminothiocarbonylamino, or diethylaminothiocarbonylamino, aminocarbonylC$_{1-6}$alkylamino, e.g. aminocarbonylmethylamino or aminocarbonylethylamino, aminothiocarbonylC$_{1-6}$alkylamino e.g. aminothiocarbonylmethylamino or aminothiocarbonylethylamino, formylaminoC$_{1-6}$ alkylsulphonylamino, e.g. formylaminomethylsulphonylamino or formyl-aminoethylsulphonylamino, thioformylaminoC$_{1-6}$alkylsulphonylamino, e.g. thioformylaminomethylsulphonylamino or thioformylethylsulphonylamino, C$_{1-6}$acylaminosulphonylamino, e.g. acetylaminosulphonylamino, C$_{1-6}$thioacylaminosulphonylamino, e.g. thioacetylaminosulphonylamino groups.

Where desired, two R$^{13}$ substituents may be linked together to form a cyclic group such as a cyclic ether, e.g. a C$_{2-6}$alkylenedioxy group such as ethylenedioxy.

It will be appreciated that where two or more R$^{13}$ substituents are present, these need not necessarily be the same atoms and/or groups. The R$^{13}$ substituents may be present at any ring carbon atom away from that attached to the rest of the molecule of formula (1). Thus, for example, in phenyl groups represented by Ar or Ar' any substituent may be present at the 2-, 3-, 4-, 5- or 6- positions relative to the ring carbon atom attached to the remainder of the molecule.

In the compounds of formula (1), when the group —(CH$_2$)$_t$Ar(L$^1$)$_n$Ar' is present in R$^4$ and/or R$^5$, the linker group L$^1$ may be any divalent linking group. Particular examples of L$^1$ groups which may be present in compounds of the invention include groups of formula —(Alk$^4$)$_r$(X$^a$)$_s$(Alk$^5$)$_t$— where Alk$^4$ and Alk$^5$ is each an optionally substituted straight or branched C$_{1-6}$alkylene, C$_{2-6}$alkenylene or C$_{2-6}$alkynylene chain optionally interrupted by one or more, e.g. one, two or three heteroatoms or carbocyclic or heteroatom-containing groups, X$^a$ is an —O— or —S— atom or a —S(O)—, —S(O)$_2$— or —N(R$^b$)— group, r is zero or the integer 1, t is zero or the integer 1 and s is zero or the integer 1,provided that when one of r, s, or t is zero at least one of the remainder is the integer 1.

The heteroatoms which may interrupt the Alk$^4$ or Alk$^5$ chains include for example —O— or —S— atoms. Carbocyclic groups include for example cycloalkyl, e.g. cyclopentyl or cyclohexyl, or cycloalkenyl e.g. cyclopentenyl or cyclohexenyl, groups. Particular heteroatom-containing groups which may interrupt Alk$^4$ or Alk$^5$ include oxygen-, sulphur- or nitrogen-containing groups such as —S(O)—, —S(O)$_2$—, —N(R$^b$)—, —C(O)—, —C(S)—, —C(NR$^b$)—, —CON(R$^b$)—, —CSN(R$^b$)—, —N(R$^b$)CO—, —N(R$^b$)CS—, —SON(R$^b$)—, —SO$_2$N(R$^b$)—, —N(R$^b$)SO—, —N(R$^b$)SO$_2$—, —N(R$^b$)SO$_2$N(R$^b$)—, —N(R$^b$)SON(R$^b$)—, or —N(R$^b$)CON(R$^b$)— groups. It will be appreciated that when the chains Alk$^4$ or Alk$^5$ are interrupted by two or more heteroatoms, carbocyclic or heteroatom-containing groups, such atoms or groups may be adjacent to one another, for example to form a group —N(R$^b$)—C(NR$^b$)—N(R$^b$)— or —O— CONH—.

Optional substituents which may be present on Alk$^4$ or Alk$^5$ chains include those described above in relation to the group R$^1$ when it is an alkyl group.

The group —(L$^1$)$_n$Ar' may be attached to the group Ar through any available carbon or heteroatoms present in the two groups. Thus, for example, when Ar is a phenyl group, —(L$^1$)$_n$Ar' may be attached through a carbon or heteroatom in —(L$^1$)$_n$Ar' to a carbon atom in Ar at the 2-, 3-, 4-, 5-, or 6- position relative to the Ar carbon atom attached to the remainder of the molecule.

In the group (L$^1$)$_n$Ar' particular examples of Alk$^4$ or Alk$^5$ include optionally substituted methylene, ethylene, propylene, butylene, ethenylene, 2-propenylene, 2-butenylene, 3-butenylene, ethynylene, 2-propynylene, 2-butynylene or 3-butynylene chains, optionally interrupted by one, two or three heteroatoms, carbocyclic or heteroatom-containing groups as described above.

Particular examples of the group —(L$^1$)$_n$Ar' include the groups —Alk$^4$Ar', —XAr', —Alk$^4$XAr' and —XAlk$^5$Ar', especially for example —CH$_2$Ar', —(CH$_2$)$_2$Ar', —(CH$_2$)$_3$Ar', —CH$_2$OCH$_2$Ar', —CH$_2$SCH$_2$Ar', —CH$_2$N(R$^b$)CH$_2$Ar', —CH═CHAr', —CH$_2$CH═CHAr', —OAr', —SAr', —N(R$^b$)Ar', —CH$_2$OAr', —CH$_2$SAr', —CH$_2$N(R$^b$)Ar', —CH$_2$OCH$_2$OAr', —OCH$_2$Ar', —O(CH$_2$)$_2$Ar', —SCH$_2$Ar', —S(CH$_2$)$_2$Ar', —N(R$^b$)CH$_2$Ar' and —N(R$^b$)(CH$_2$)$_2$Ar'. In these particular groups, Ar' may be as generally described herein and as particularly described below.

In general, and in the particular groups just mentioned, Alk in Ar' may be an optionally substituted methylene, ethylene, n-propylene, i-propylene, n-butylene, s-butylene, t-butylene, ethenylene, 2-propenylene, 2-butenylene, 3-butenylene, ethynylene, 2-propenylene, 2-butynylene, or 3-butynylene chain optionally interrupted by one, two or three —O— or —S— atoms or —S(O)—, —S(O)$_2$— or —N(R$^b$)— groups. Optional substituents which may be present include one or more halogen atoms, e.g. fluorine, chlorine, bromine or iodine atoms, or hydroxyl or C$_{1-6}$alkoxy e.g. C$_{1-3}$alkoxy such as methoxy or ethoxy groups. The group Alk$^1$ when present in Ar' may also be as just described for Alk, but will clearly be an alkyl, alkenyl or alkynyl group, rather than a corresponding alkylene, alkenylene or alkynylene chain.

Particular examples of the group Ar' include optionally substituted C$_{6-12}$aryl or C$_{1-9}$heteroaryl groups, especially optionally substituted phenyl or pyridyl groups, or, in particular, —CO(Alk)$_m$Ph (where Ph is an optionally substituted phenyl group), —SONH(Alk)$_m$Ph, —SO$_2$N(Alk$^1$)(Alk)$_m$Ph, —SO$_2$N[(Alk)$_m$Ph]$_2$, —CONH(Alk)$_m$Ph, —CON(Alk$^1$)(Alk)$_m$Ph, —CON[(Alk)$_m$Ph]$_2$, —NAlk$^1$SO$_2$(Alk)$_m$Ph, —NHSO$_2$N(Alk$^1$)(Alk)$_m$Ph, —NAlk$^1$SO$_2$Alk$^1$ (Alk)$_m$Ph, —NHSO$_2$N[(Alk)$_m$Ph]$_2$, —NAlk$^1$SO$_2$N[(Alk)$_m$Ph]$_2$, —NHC(O)(Alk)$_m$Ph, —NAlk$^1$CO(Alk)$_m$Ph, —NC(O)N[(Alk)$_m$Ph]$_2$, —NHC(O)NH(Alk)$_m$Ph, —NAlk$^1$C(O)NH(Alk)$_m$Ph, —NHC(O)N(Alk$^1$)(Alk)$_m$Ph, —NAlk$^1$C(O)N(Alk$^1$)(Alk)$_m$Ph, —NHC(O)O(Alk)$_m$Ph, —NAlk$^1$C(O)O(Alk)$_m$Ph, —C(S)NH(Alk)$_m$Ph, —C(S)N(Alk$^1$)(Alk)$_m$Ph, —N(S)N[(Alk)$_m$Ph]$_2$, —NHC(S)(Alk)$_m$Ph, —N(Alk$^1$)C(S)(Alk)$_m$Ph, —N[C(S)(Alk)$_m$Ph]$_2$, —NHC(S)NH(Alk)$_m$Ph, —NAlk$^1$C(S)NH(Alk)$_m$Ph, —NHC(S)N(Alk$^1$)(Alk)$_m$Ph, or —N(Alk$^1$)C(S)N(Alk$^1$)(Alk)$_m$Ph groups. In these groups, the groups Alk and Alk$^1$ may in particular each be a methylene or ethylene, and a methyl or ethyl group respectively and m may be zero or in particular 1.

When in R$^4$ and/or R$^5$ a —NHet group is present this may be for example a pyrrolidinyl, pyrazolidinyl, piperidinyl, morpholinyl, piperazinyl or thiomorpholinyl group. Optional substituents that may be present in such groups include R$^{13}$ substituents described above in relation to Ar or Ar' groups.

When in R$^4$ and/or R$^5$ a Het' group is present this may be for example a pyrrolidinyl, pyrazolidinyl, piperidinyl, morpholinyl, piperazinyl, thiomorpholinyl, cyclopentyl, or cyclohexyl group. Optional substituents that may be present on such groups include R$^{13}$ substituents described above.

In the compounds of formula (1), when an ester group is present, for example a group CO$_2$R$^8$ or —CO$_2$Alk$^3$ this may advantageously be a metabolically labile ester.

In the —(CH$_2$)$_r$ArN(R$^b$)CX$^1$N(R$^b$)L$^2$(Alk)$_m$Ar group present as R$^4$ and/or R$^5$ in compounds of formula (1) the divalent linking group represented by L$^2$ may be for example a —S(O)—, —S(O)N(R$^b$)—, —S(O)$_2$—, —S(O)$_2$N(R$^b$)—, —C(O)—, —C(O)N(R$^b$)—, —C(S)— or —C(S)N(R)— group. All the other groups represented by —(CH$_2$)$_r$, Ar, R$^b$ X$^1$, and (Alk)$_m$ may be as generally and particularly discussed above.

Particular examples of R$^4$ and/or R$^5$ groups of these types include —ArN(R$^b$)CONHSO$_2$(Alk)$_m$Ar and —ArN(R$^b$)CONHSO$_2$N(R$^2$)(Alk)$_m$Ar groups, especially where Ar is an optionally substitued phenyl group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1) the group =W— is preferably a =C(Y)— group. In compounds of this type Y is preferably a —XR$^a$ group where X is —O— and R$^a$ is an optionally substituted ethyl group or, especially, an optionally substituted methyl group. Especially useful substituents which may be present on R$^a$ groups include one, two or three fluorine or chlorine atoms.

One particularly useful group of compounds of the invention has the formula (1) where L is a group —XR. In compounds of this type X is preferably —O—. The group R in these compounds is preferably an optionally substituted cycloalkyl group, particularly an optionally substituted cyclopentyl group, and is, especially a cyclopentyl group.

In another group of compounds of formula (1) L is preferably a —CH=C(R$^1$)(R$^2$) group. In compounds of this type R$^1$ and R$^2$ are preferably linked together with the C atom to which they are attached to form an optionally substituted cycloalkyl or cycloalkenyl group, especially a substituted cyclopentyl or cyclohexyl or, especially, a cyclopentyl or cyclohexyl group.

The groups R$^4$ and R$^5$ in compounds of formula (1) is each, independently, preferably a CH$_2$Ar, —CH$_2$Ar(L$^1$)$_n$Ar' or —CH$_2$ArN(R$^b$)CX$^1$N(R$^b$)L$^2$(Alk)$_m$Ar group or especially an —Ar, Ar—Ar', ArL$^1$Ar' or —ArN(R$^b$)CX$^1$N(R$^b$)L$^2$(Alk)$_m$Ar group, with the proviso mentioned in connection with formula (1). In one preference the group R$^4$ is especially a —ArN(R$^b$)CX$^1$N(R$^b$)L$^2$(Alk)$_m$Ar group and R$^5$ is an —Ar group. Particularly useful R$^4$ or R$^5$ groups of these types include those groups in which Ar or Ar' is a monocyclic aryl group optionally containing one or more heteroatoms selected from oxygen, sulphur, or, in particular, nitrogen atoms, and optionally substituted by one, two, three or more R$^{13}$ substituents. In these compounds, when the group represented by Ar or Ar' is a heteroaryl group it is preferably a nitrogen-containing monocyclic heteroaryl group, especially a six-membered nitrogen-containing heteroaryl group. Thus, in one preferred example, the groups R$^4$ and R$^5$ may each contain a six-membered nitrogen-containing heteroaryl Ar or Ar' group. In another preferred example R$^4$ may contain a monocyclic aryl group or a monocyclic or bicyclic heteroaryl group Ar or Ar' containing one or more oxygen, sulphur or nitrogen atoms and R$^5$ may contain a six-membered nitrogen-containing heteroaryl group Ar or Ar'. In these examples, the six-membered nitrogen-containing heteroaryl group may be an optionally substituted pyridyl, pyridazinyl, pyrimidinyl, pyrazinyl or imidazolyl group. Particular examples include optionally substituted 2-pyridyl, 3-pyridyl, 5-imidazolyl, or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic or bicyclic heteroaryl group containing one or more oxygen, sulphur or nitrogen atom may be an optionally substituted 2-furyl, 3-furyl, 2-thienyl, 3-thienyl, 2-thiazolyl, 2-benzo(b)thiophenyl, 2-benzo(b)furyl or 4-isoquinolinyl group.

In another preference relating to $R^4$ groups of the just mentioned particular types, Ar' is a —NHC(O)NH(Alk)$_m$Ph (where Ph is as just described, —NHCH$_3$C(O)NH(Alk)$_m$Ph, —NHC(O)N(CH$_3$)(Alk)$_m$Ph, —N(CH$_3$)C(O)N(CH$_3$)(Alk)$_m$ Ph, —CO(Alk)$_m$Ph, —NHSO$_2$NH(Alk)$_m$Ph, —N(CH$_3$)SO$_2$NH(Alk)$_m$Ph, —N(CH$_3$)SO$_2$N(CH$_3$)(Alk)$_m$Ph, —NHCO(Alk)$_m$Ph, —N(CH$_3$)CO(Alk)$_m$Ph or —NHSO$_2$(Alk)$_m$Ph group.

In general in compounds of formula (1) when $R^4$ and/or $R^5$ contains a substituted phenyl group it may be for example a mono-, di- or trisubstituted phenyl group in which the substituent is an atom or group $R^{13}$ as defined above. When the $R^4$ and/or $R^5$ group contains a monosubstituted phenyl group the substituent may be in the 2-, or preferably 3-, or especially 4-position relative to the ring carbon atom attached to the remainder of the molecule. When the $R^4$ and/or $R^5$ group contains a disubstituted phenyl group, the substituents may be in the 2,6 position relative to the ring carbon atom attached to the remainder of the molecule.

Particularly useful substituents $R^{13}$ which may be present on Ar groups in $R^4$ and $R^5$, especially on phenyl groups, include halogen atoms or alkyl, haloalkyl, amino, substituted amino, nitro, —NHSO$_2$NH$_2$, —NHSO$_2$NHCH$_3$, —NHSO$_2$N(CH$_3$)$_2$, —NHCOCH$_3$, —NHC(O)NH$_2$, —NCH$_3$C(O)NH$_2$, —NHC(O)NHCH$_3$, —NHC(O)NHCH$_2$CH$_3$, or —NHC(O)N(CH$_3$)$_2$ groups, each of said atoms or groups being optinally separated from the remainder of the Ar group by a group Alk$^2$ as defined above.

When in compounds of formula (1) $R^4$ and/or $R^5$ contains a substituted pyridyl group it may be for example a mono-or disubstituted pyridyl group, such as a mono- or disubstituted 2-pyridyl, 3-pyridyl or especially 4-pyridyl group substituted by one or two atoms or groups $R^{13}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particularly useful group of compounds of formula (1) has the formula (2):

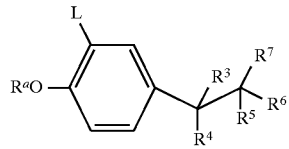

(2)

where —L is a OR, where R is an optionally substituted cycloalkyl group, —CH=C(R$^1$)(R$^2$) or —CH$_2$CH(R$^1$)(R$^2$) group where $R^1$ and $R^2$ are linked together with the carbon atom to which they are attached to form a cycloalkyl group; $R^a$ is an optionally substituted alkyl group and $R^3$, $R^4$, $R^5$, $R^6$ and $R^7$ are as defined for formula (1); and the salts, solvates, hydrates, prodrugs and N-oxides thereof.

In the compounds of formulae (1) or (2) one preferred group of compounds are those where the group $R^3$ is a hydrogen atom; the group $R^6$ is a methyl group, or especially a hydrogen atom; the group $R^7$ is a methyl group, or especially a hydrogen atom; and $R^4$ and $R^5$ are as defined for formula (1). In compounds of this type $R^6$ and $R^7$ is each especially a hydrogen atom.

In general in compounds of formulae (1) or (2) $R^3$, $R^6$ and $R^7$ is each especially a hydrogen atom, $R^5$ is in particular a —(CH$_2$)$_r$Ar group, especially an optionally substituted pyridyl group, especially a 4-pyridyl group. The group $R^4$ in compounds of these types is preferably an —ArN(R$^b$)CX$^1$N(R$^b$)L$^2$(Alk)$_m$Ar group, particularly where each Ar group is a monocyclic aryl group optionally containing one or more heteroatoms selected from oxygen, sulphur or, especially, nitrogen atoms. Particularly useful $R^4$ groups are those of formula —ArN(R$^b$)CX$^1$N(R$^b$)S(O)$_2$(Alk)$_m$Ar or —ArN(R$^b$)CX$^1$N(R$^b$)S(O)$_2$N(R$^b$)(Alk)$_m$Ar, especially where each Ar group is an optionally substituted phenyl group. Particular examples of such groups include —ArNHCONHS(O)$_2$Ar, —ArNHCSNHS(O)$_2$Ar, —ArNHCONHS(O)$_2$NHAr and —ArNHCSNHS(O)$_2$NHAr, especially where in each instance Ar is an optionally substituted phenyl group as defined herein. In general in these compounds, when Ar is a phenyl group the —N(R$^b$)CX$^1$N(R$^b$)L$^2$(Alk)$_m$Ar group is preferably attached to this group at the 3- or 4-position of the phenyl ring relative to the point of attachment of the ring to the remainder of the molecule of formula (1).

In one particular group of compounds of formulae (1) or (2) $R^4$ is preferably a —ArNHCONHS(O)$_2$Ar" group wherein Ar is a phenyl group and Ar" is an optionally substituted phenyl group. In these compounds the —NHCONHS(O)$_2$Ar" group is preferably attached to the Ar group at the 3- or 4-position of the phenyl ring as explained above. In this particular group of compounds the other groups W, L, $R^3$, $R^5$, $R^6$ and $R^7$ may be as generally or particularly defined above.

Particularly useful compounds according to the invention are:

(R)-N-[4-{1-(3-cyclopentyloxy-4-methoxyphenyl)-2-(4-pyridyl)ethyl}phenyl]-N'-(phenylsulphonyl) urea;

(R)-N-[4-{1-(3-cyclopentyloxy-4-methoxyphenyl)-2-(4-pyridyl)ethyl}phenyl]-N'-(methylphenylsulphonyl) urea; and (R)-N-[4-{1-(3-cyclopentyloxy-4-methoxyphenyl)-2-(4-pyridyl)ethyl}phenyl]-N'-(4-chlorophenylsulphonyl) urea;

and the salts, solvates, hydrates, prodrugs and N-oxides thereof.

Compounds according to the invention are selective and potent inhibitors of PDE IV and advantageously have improved metabolic stability. The ability of the compounds to act in this way may be simply determined by the tests described in the Examples hereinafter.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formulae (1) and (2) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administratino by inhalation or insufflation.

The compounds according to the invention may be prepared by the following processes. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981].

Thus according to a further aspect of the invention a compound of formula (1) may be prepared by reaction of a corresponding intermediate compound of formula (1) wherein $R^4$ and/or $R^5$ is a —$(CH_2)_r$ArNHR$^b$ group with an isocyanate Ar(Alk)$_m$L$^2$N=C=O or isothiocyanate Ar(Alk)$_m$ L$^2$N=C=S. The reaction may be performed in a solvent, for example an organic solvent such as a halogenated hydrocarbon, e.g. dichloromethane, at around -0° C. to around ambient temperature.

In a variation of this process the starting intermediate amine of formula (1) may first be treated with phosgene in the presence of a base, e.g. an organic amine such as triethylamine, and subsequently reacted with an amine Ar(Alk)$_m$L$^2$NHR$^b$ to yield the desired compound of formula (1) wherein $R^4$ and/or $R^5$ contains a urea group. The reaction may be carried out in an organic solvent such as a halogenated hydrocarbon, e.g dichloromethane, at from around 0° C. to ambient temperature.

The intermediate amines of formula (1) for use as starting materials in these reactions are either described in International Patent Specification Nos. WO94/14742 and WO95/17386 or International patent application No. PCT/GB95/

01459, or may be obtained using the processes described therein from known starting materials. The intermediate isocyanates, isothiocyanates and amines also for use in these processes are readily available known compounds or may be prepared from known starting materials using methods analogous to those used for the preparation of the known compounds.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography.

Alternatively, a particular enantiomer may be obtained by using an appropriate chiral intermediate in one of the processes described above. Chiral intermediates may be obtained in particular by use of the enantioselective process described in International Patent Specification No. WO95/17386.

The following Examples illustrate the invention, and describe the preparation of the following compounds:

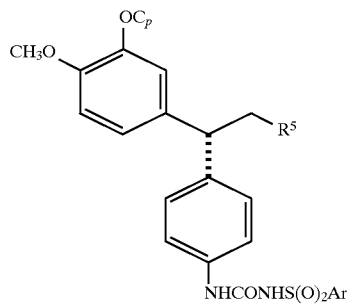

where Cp is cyclopentyl, $R^5$ is 4-pyridyl and Ar is:

EXAMPLE 1

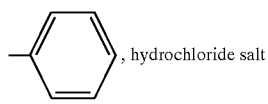, hydrochloride salt

EXAMPLE 2

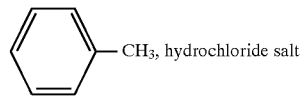 CH₃, hydrochloride salt

EXAMPLE 3

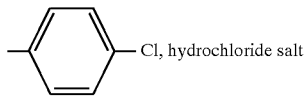 Cl, hydrochloride salt

EXAMPLE 1

(R)-N-[4-{1-(3-Cyclopentyloxy-4-methoxyphenyl)-2-(4-pyridyl)ethyl}-phenyl]-N'-(phenylsulphonyl) urea, hydrochloride Benzenesulphonylisocyanate (205 µl) was added dropwise to a solution of 4-[1-(R)-(3-cyclopentyloxy-4-methoxyphenyl)-2-(4-pyridyl)ethyl]aniline (500 mg prepared as described in International Patent specification No. WO95/17386) in dichloromethane (10 ml) under nitrogen at room temperature. The mixture was stirred or 30 min at this temperature and the solvent then removed in vacuo to yield a yellow gum. Trituration with ether furnished a pale yellow solid (the free base of the title compound which was disolved in dichloromethane (5 ml) and treated with ethereal HCl to afford a yellow solid. Subsequent recrystallisation of the solid from methanol yielded the title compound (450 mg) as an off white solid $\delta_H$ (CD₃OD) 1.40–1.90 (8H, br m), 3.64 (2H, d, J 9 Hz), 3.72 (3H, s), 4.34 (1H, t, J 9 Hz), 4.72 (1H, m), 6.75 (3H, d+d+s), 7.20 (4H, d+d), 7.50–7.75 (3H, m), 7.72 (2H, d, J 8 Hz), 8.00 (2H, d, J 8 Hz), and 8.55 (2H, d, J 8 Hz).

The following compounds were prepared in a similar manner to the compound of Example 1:

EXAMPLE 2

(R)-N-[4-{1-(3-Cyclopentyloxy-4-methoxyphenyl)-2-(4-pyridyl)ethyl}-phenyl]-N'-(methylphenylsulphonyl) urea, hydrochloride From the starting aniline (1.0 g) used in Example 1 and p-toluenesulphonylisocyanate (507 mg) in dichloromethane (20 ml) at 0°–5° C. to yield the free base of the title compound (1.29 g) as a white solid $\delta_H$ (CDCl₃) 149–1.95 (8H, m), 2.4 (3H, s), 3.28 (2H, d, J 7.9 Hz), 3.6–3.9 (1H, br s), 3.78 (3H, s), 4.11 (1H, t, J 6.0 Hz), 4.65 (1H, m), 6.62–6.78 (3H, m), 6.95 (2H, d, J 6.06 Hz), 7.1 (2H, d, J 8.57 Hz), 7.26 (4H, m), 7.79 (2H, d, J 8.37 Hz), and 8.40 (3H, m). m/z (ESI) (MH+586, 100%).

The solid on treatment with ethereal HCl gave the title compound as an off white solid. (Found: C, 62.04; H, 5.90; N, 6.39. C₃₃H₃₅N₃O₅S. HCl. H₂O requires C, 61.91; H, 5.98, N, 6.56%) $\delta_H$ (CD₃OD) 1.45–1.85 (8H, m), 2.38 (3H, s), 3.6 (2H, d, J 6.0 Hz), 3.7 (3H, s), 4.3 (1H, m), 4.68 (1H, br, s), 6.68–6.8 (3H, m), 7.1–7.45 (6H, m), 7.7–7.9 (4H, m) and 8.52 (2H, br s).

EXAMPLE 3

(R)-N-[4-{1-(3-Cyclopentyloxy-4-methoxyphenyl)-2-(4-pyridyl)ethyl}-phenyl]-N'-(4-chlorophenylsulphonyl)urea, hydrochloride From the starting aniline (1.0 g) used in Example 1 and 4-chlorobenzenesulphonylisocyanate (0.384 ml) in dichloromethane (20 ml) at 0°–5° C. to yield the free base of the title compound (1.49 g) as a white solid, $\delta_H$ ($CD_{Cl3}$) 1.43–1.9 (8H, m), 3.3 (2H, d, J 7.82 Hz), 3.77 (3H, s), 4.09 (1H, t, J 7.75 Hz, J' 7.96 Hz), 4.69 (1H, m), 5.59 (1H, br s), 6.62–6.8 (3H, m), 6.95–7.1 (4H, m), 7.15–7.4 (4H, m), 7.88 (2H, d, J 7.1 Hz), 8.36 (2H, d, J 6.0 Hz) and 8.50 (1H, s); m/z (ESI) (MH+505 100%)

The solid on treatment with ethereal HCl gave the title compound as a light yellow solid (Found: C, 58.33, H, 5.17, N, 6.12. $C_{32}H_{32}ClN_3O_5S$. HCl. 0.75 $H_2O$ requires C, 58.58, H, 5.30, N, 6.41%) $\delta_H$ ($CD_3OD$) 1.42–1.8 (8H, m), 3.12 (2H. d, J 6.0 Hz), 3.68 (3H, s), 4.3 (1H, m), 4.67 (1H, m), 6.72 (3H, m), 7.1–7.25 (4H, m), 7.45–7.55 (2H, m), 7.77 (2H, d, J 3.0 Hz), 7.94 (2H, d, J 8.7 Hz) and 8.55 (2H, d, J 3.0 Hz); m/z (ESI) (MH+606 100%.

The advantageous pharmacological properties of the compounds according to the invention may be demonstrated in the following in vitro and in vivo tests:

1. Isolated Recombinant Human PDE IVA Enzyme

A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IVA, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 $\mu$l of standard mixture containing (final concentrations): 50 mM 2-[[tris(hydroxymethyl)methyl]amino]-1-ethanesulphonic acid (TES) —NaOH buffer (pH 7.5), 10 mM $MgCl_2$, 0.1 $\mu$M [$^3$H]-cAMP and vehicle or various concentrations of the test compounds. The reaction was initiated by addition of enzyme and conducted at 30° C. for between 5 to 30 min. The reaction was terminated by addition of 50 $\mu$l 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction. Results were expressed as $IC_{50}$ values.

Using this procedure, the compounds according to the invention had $IC_{50}$ values of 4 nM (compound of Example 1), 13.9 nM (compound of Example 2) and 17.6 nM (compound of Example 3).

The compounds of the Examples had little or no activity against other isolated PDE isoenzymes (specifically PDE I, II, III or V—see WO 94/14742 for experimental details) at concentrations up to 100 $\mu$M, thus illustrating the selectivity of their action against PDE IV.

2. Rat Hepatocyte Metabolism

The improved metabolic stability of the compounds according to the invention was demonstrated in a conventional rat hepatocyte model in which rat hepatocytes were cultured in the presence of test compound. The quantity of compound remaining after a fixed period of time was then determined using mass spectroscopy.

Thus in one such test the compound of Example 1 was compared with a related compound particularly described in International Patent Specification No. WO94/14742 in which the phenylsulphonyl group in the compound of Example 1 is replaced by a hydrogen atom. After 3 h the percentage of each compound remaining was:

Compound of Example 1—56%
WO 94/14732 comparison compound—3%.

The WO94/14742 compound had been extensively metabolised whereas over 50% of the compound of the invention remained after 3 h, illustrating the advantageous in vitro metabolic stability of the compound.

The same two compounds were also administered orally to squirrel monkeys at 10 mg/kg p.o,. and the plasma levels of each determined. After 1 h the WO94/14732 compound was present at 1 $\mu$g/ml whereas after 30 min the compound of Example 1 was present at 34 $\mu$g/ml, thus illustrating the good oral availability of the compound.

We claim:

1. A compound of formula (1):

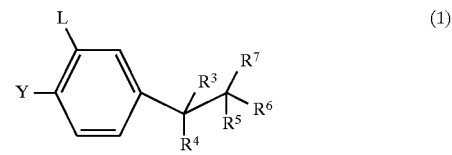

wherein:

Y is halogen or an alkyl or —$XR^a$ group;

X is —O—, —S(O)$_p$— or —N($R^b$)—, where p is zero or an integer 1 or 2;

L is —XR, —C($R^{11}$)=C($R^1$)($R^2$) or —(CHR$^{11}$)$_n$CH($R^1$)($R^2$), where n is zero or the integer 1;

each of $R^a$ and $R^b$ is independently hydrogen or an optionally substituted alkyl group;

R is an optionally substituted alkyl, alkenyl, cycloalkyl or cycloalkenyl group;

each of $R^1$ and $R^2$, which may be the same or different, is hydrogen, fluorine, —CN, —$NO_2$, or an optionally substituted alkyl, alkenyl, alkynyl, alkoxy, alkylthio, —$CO_2R^8$, —$CONR^9R^{10}$ or —$CSNR^9R^{10}$ group, or $R^1$ and $R^2$, together with the carbon atom to which they are attached, are linked to form an optionally substituted cycloalkyl or cycloalkenyl group;

$R^3$ is hydrogen, fluorine, hydroxy or an optionally substituted straight or branched alkyl group;

$R^4$ is hydrogen, —(CH$_2$)$_t$Ar, —(CH$_2$)$_t$—Ar—(L$^1$)$_n$—Ar' or —(CH$_2$)$_t$ArN(R$^b$)CX$^1$N(R$^b$)L$^2$(Alk)$_m$Ar, where t is zero or an integer 1, 2 or 3;

$R^5$ is —(CH$_2$)$_t$Ar, —(CH$_2$)$_t$—Ar—(L$^1$)$_n$—Ar' or —CH$_2$)$_t$ArN(R$^b$)CX$^1$N(R$^b$)L$^2$(Alk)$_m$Ar;

$R^b$ is hydrogen or an optionally substituted alkyl group;

$R^6$ is hydrogen, fluorine, or an optionally substituted alkyl group;

$R^7$ is hydrogen, fluorine, an optionally substituted straight or branched alkyl group, —OR$^c$, where R$^c$ is hydrogen or an optionally substituted alkyl or alkenyl group, or a formyl, alkoxyalkyl, alkanoyl, carboxamido or thiocarboxamido group;

each of $R^8$, $R^9$ and $R^{10}$, which may be the same or different, is hydrogen or an optionally substituted alkyl, aralkyl or aryl group;

$R^{11}$ is hydrogen, fluorine or a methyl group;

$X^1$ is an oxygen or sulphur atom;

$L^1$ and $L^2$ are independently divalent linking groups;

Ar is a monocyclic or bicyclic aryl group, optionally containing one or more heteroatoms selected from oxygen, sulphur and nitrogen atoms;

Ar' is Ar, —CO(Alk)$_m$Ar, —SO$_2$(Alk)$_m$Ar, —SO$_2$NH(Alk)$_m$Ar, —SO$_2$N(Alk$^1$)(Alk)$_m$Ar, —SO$_2$N((Alk)$_m$Ar)$_2$, —CONH(Alk)$_m$Ar, —CON(Alk$^1$)(Alk)$_m$Ar, —CON((Alk)$_m$Ar)$_2$, —N(Alk$^1$)SO$_2$(Alk)$_m$Ar, —NHSO$_2$(Alk)$_m$Ar, —N(SO$_2$(Alk)$_m$Ar)$_2$, —NHSO$_2$NH(Alk)$_m$Ar, —N(Alk$^1$)SO$_2$NH(Alk)$_m$Ar, —NHSO$_2$N(Alk$^1$)(Alk)$_m$Ar, —N(Alk$^1$)SO$_2$N(Alk$^1$)(Alk)$_m$Ar, —NHSO$_2$N((Alk)$_m$Ar)$_2$, —N(Alk$^1$)SO$_2$N((Alk)$_m$Ar)$_2$, —NHC(O)(Alk)$_m$Ar, —N(Alk$^1$)C(O)(Alk)$_m$Ar, —N(C(O)(Alk)$_m$Ar)$_2$, —NHC(O)NH(Alk)$_m$Ar, —N(Alk$^1$)C(O)NH(Alk)$_m$Ar, —NHC(O)N(Alk$^1$)(Alk)$_m$Ar, —NAlk$^1$C(O)N(Alk$^1$)(Alk)$_m$Ar, —NHC(O)O(Alk)$_m$Ar, —N(Alk$^1$)C(O)O(Alk)$_m$Ar, —C(S)NH(Alk)$_m$Ar, —C(S)N(Alk$^1$)(Alk)$_m$Ar, —C(S)N(Alk$^1$)(Alk)$_m$Ar, —C(S)N((Alk)$_m$Ar)$_2$, —NHC(S)(Alk)$_m$Ar, —N(Alk$^1$)C(S)(Alk)$_m$Ar, —N(C(S)(Alk)$_m$Ar)$_2$, —NHC(S)NH(Alk)$_m$Ar, —N(Alk$^1$)C(S)NH(Alk)$_m$Ar, —NHC(S)N(Alk$^1$)(Alk)$_m$Ar, —N(Alk$^1$)C(S)N(Alk$^1$)(Alk)$_m$Ar, —SO$_2$(Alk)$_m$NHet, —CO(Alk)$_m$NHet, —CS(Alk)$_m$NHet, —NHSO$_2$(Alk)$_m$NHet, —NHC(O)(Alk)$_m$NHet, —NHC(S)(Alk)$_m$NHet, —SO$_2$NH((Alk)$_m$ Het'), —CONH((Alk)$_m$Het'), —CSNH((Alk)$_m$Het'), —NHSO$_2$NH((Alk)$_m$Het'), —NHC(O)NH(Alk)$_m$ (Het') or —NHC(S)NH(Alk)$_m$(Het');

m is zero or the integer 1;

Alk is an optionally substituted, straight or branched C$_{1-6}$alkylene, C$_{2-6}$alkenylene or C$_{2-6}$alkynylene chain optionally interrupted by one, two or three —O— or —S— atoms or —S(O)$_q$— or —N(R$^b$)— groups, where q is an integer 1 or 2;

Alk$^1$ is an optionally substituted, straight or branched C$_{1-6}$alkyl, C$_{2-6}$alkenyl or C$_{2-6}$alkynyl chain optionally interrupted by one, two or three —O— or —S— atoms or —S(O)$_q$— or —N(R$^b$)— groups;

NHet is an optionally substituted C$_{5-7}$heterocyclic amino group optionally containing one or more additional —O— or —S— atoms or —N(R$^b$)—, —CO— or —CS— groups;

Het' is an optionally substituted C$_{5-7}$monocyclic carbocyclic group optionally containing one or more —O— or —S— atoms or —N(R$^b$)— groups:

or a salt, solvate, hydrate, prodrug or N-oxide thereof; with the proviso that at least one of $R^4$ and $R^5$ is —(CH$_2$)$_t$ArN(R$^b$)CX$^1$N(R$^b$)L$^2$(Alk)$_m$Ar.

2. A pharmaceutical composition comprising a compound of formula (1):

wherein:

Y is halogen or an alkyl or —XR$^a$ group;

X is —O—, —S(O)$_p$— or —N(R$^b$)—, where p is zero or an integer 1 or 2;

L is —XR, —C(R$^{11}$)=C(R$^1$)(R$^2$) or —(CHR$^{11}$)$_n$CH(R$^1$)(R$^2$), where n is zero or the integer 1;

each of R$^a$ and R$^b$ is independently hydrogen or an optionally substituted alkyl group;

R is an optionally substituted alkyl, alkenyl, cycloalkyl or cycloalkenyl group;

each of $R^1$ and $R^2$, which may be the same or different, is hydrogen, fluorine, —CN, —NO$_2$, or an optionally substituted allyl, alkenyl, alkynyl, alkoxy, alkylthio, —CO$_2$R$^8$, —CONR$^9$R$^{10}$ or —CSNR$^9$R$^{10}$ group, or $R^1$ and $R^2$, together with the carbon atom to which they are attached, are linked to form an optionally substituted cycloalkyl or cycloalkenyl group;

$R^3$ is hydrogen, fluorine, hydroxy or an optionally substituted straight or branched alkyl group;

$R^4$ is hydrogen, —(CH$_2$)$_t$Ar, —(CH$_2$)$_t$—Ar—(L$^1$)$_n$—Ar' or —(CH$_2$)$_t$ArN(R$^b$)CX$^1$N(R$^b$)L$^2$(Alk)$_m$Ar, where t is zero or an integer 1, 2 or 3;

$R^5$ is —(CH$_2$)$_t$Ar, —(CH$_2$)$_t$—Ar—(L$^1$)$_n$—Ar' or —(CH$_2$)$_t$ArN(R$^b$)CX$^1$N(R$^b$)L$^2$(Alk)$_m$Ar;

$R^6$ is hydrogen, fluorine, or an optionally substituted alkyl group;

$R^7$ is hydrogen, fluorine, an optionally substituted straight or branched alkyl group, —OR$^c$, where R$^c$ is hydrogen or an optionally substituted alkyl or alkenyl group, or a formyl, alkoxyalkyl, alkanoyl, carboxamido or thiocarboxamido group;

each of $R^8$, $R^9$ and $R^{10}$, which may be the same or different, is hydrogen or an optionally substituted alkyl, aralkyl or aryl group;

$R^{11}$ is hydrogen, fluorine or a methyl group;

$X^1$ is an oxygen or sulphur atom;

$L^1$ and $L^2$ are independently divalent linking groups;

Ar is a monocyclic or bicyclic aryl group, optionally containing one or more heteroatoms selected from oxygen, sulphur and nitrogen atoms;

Ar' is Ar, —CO(Alk)$_m$Ar, —SO$_2$(Alk)$_m$Ar, —SO$_2$NH(Alk)$_m$Ar, —SO$_2$N(Alk$^1$)(Alk)$_m$Ar, —SO$_2$N((Alk)$_m$Ar)$_2$, —CONH(Alk)$_m$Ar, —CON(Alk$^1$)(Alk)$_m$Ar, —CON((Alk)$_m$Ar)$_2$, —N(Alk$^1$)SO$_2$(Alk)$_m$Ar, —NHSO$_2$(Alk)$_m$Ar, —N(SO$_2$(Alk)$_m$Ar)$_2$, —NHSO$_2$NH(Alk)$_m$Ar, —N(Alk$^1$)SO$_2$NH(Alk)$_m$Ar, —NHSO$_2$N(Alk$^1$)(Alk)$_m$Ar, —N(Alk$^1$)(Alk)$_m$Ar, —NHSO$_2$N((Alk)$_m$Ar)$_2$, —N(Alk$^1$)SO$_2$N(Alk)$_m$Ar)$_2$, —NHC(O)(Alk)$_m$Ar, —N(Alk$^1$)C(O)(Alk)$_m$Ar, —N(C(O)(Alk)$_m$Ar)$_2$, —NHC(O)NH(Alk)$_m$Ar, —N(Alk$^1$)C(O)NH(Alk)$_m$Ar, —NHC(O)N(Alk$^1$)(Alk)$_m$Ar, —NAlk$^1$C(O)N(Alk$^1$)(Alk)$_m$Ar, —NHC(O)O(Alk)$_m$Ar, —N(Alk$^1$)C(O)O(Alk)$_m$Ar, —C(S)NH(Alk)$_m$Ar, —C(S)N(Alk$^1$)(Alk)$_m$Ar, —C(S)N(Alk$^1$)(Alk)$_m$Ar, —C(S)N((Alk)$_m$Ar)$_2$, —NHC(S)(Alk)$_m$Ar, —N(Alk$^1$)C(S)(Alk)$_m$Ar, —N(C(S)(Alk)$_m$Ar)$_2$, —NHC(S)NH(Alk)$_m$Ar, —N(Alk$^1$)C(S)NH(Alk)$_m$Ar, —NHC(S)N(Alk$^1$)(Alk)$_m$Ar, —N(Alk$^1$)C(S)N(Alk$^1$)(Alk)$_m$Ar, —SO$_2$(Alk)$_m$NHet, —CO(Alk)$_m$NHet, —CS(Alk)$_m$NHet, —NHSO$_2$(Alk)$_m$NHet, —NHC(O)(Alk)$_m$ NHet, —NHC(S)(Alk)$_m$NHet, —SO$_2$NH((Alk)$_m$ Het'), —CONH((Alk)$_m$Het'), —CSNH((Alk)$_m$Het'), —NHSO$_2$NH((Alk)$_m$Het'), —NHC(O)NH(Alk)$_m$(Het') or —NHC(S)NH(Alk)$_m$(Het');

m is zero or the integer 1;

Alk is an optionally substituted, straight or branched C$_{1-6}$alkylene, C$_{2-6}$alkenylene or C$_{2-6}$alkynylene chain optionally interrupted by one, two or three —O— or —S— atoms or —S(O)$_q$— or —N(R$^b$)— groups, where q is an integer 1 or 2;

Alk$^1$ is an optionally substituted, straight or branched C$_{1-6}$alkyl, C$_{2-6}$alkenyl or C$_{2-6}$alkynyl chain optionally interrupted by one, two or three —O— or —S— atoms or —S(O)$_q$— or —N(R$^b$)— groups;

NHet is an optionally substituted C$_{5-7}$heterocyclic amino group optionally containing one or more additional —O— or —S— atoms or —N(R$^b$)—, —CO— or —CS— groups;

Het' is an optionally substituted C$_{5-7}$monocyclic carbocyclic group optionally containing one or more —O— or —S— atoms or —N(R$^b$)— groups;

or a salt, solvate, hydrate, prodrug or N-oxide thereof; with the proviso that at least one of R$^4$ and R$^5$ is —(CH$_2$)$_t$ArN(R$^b$)CX$^1$N(R$^b$)L$^2$(Alk)$_m$Ar;

together with one or more pharmaceutically acceptable carriers, excipients or diluents.

3. A compound of formula (2):

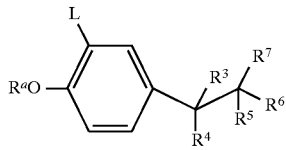

(2)

wherein:

L is —OR, —CH=C(R$^1$)(R$^2$) or —CH$_2$CH(R$^1$)(R$^2$);

R$^a$ is an optionally substituted alkyl group;

R is an optionally substituted cycloalkyl group;

R$^1$ and R$^2$, together with the carbon atom to which they are attached, are linked to form an optionally substituted cycloalkyl group;

R$^3$ is hydrogen, fluorine, hydroxy or an optionally substituted straight or branched alkyl group;

R$^4$ is hydrogen, —(CH$_2$)$_t$Ar, —(CH$_2$)$_t$—Ar—(L$^1$)$_n$—Ar' or —(CH$_2$)$_t$ArN(R$^b$)CX$^1$N(R$^b$)L$^2$(Alk)$_m$Ar, where t is zero or an integer 1, 2 or 3 and n and m are independently zero or the integer 1;

R$^b$ is hydrogen or an optionally substituted alkyl group;

R$^5$ is —(CH$_2$)$_t$Ar, —(CH$_2$)$_t$—Ar—(L$^1$)$_n$—Ar' or —(CH$_2$)$_t$ArN(R$^b$)CX$^1$N(R$^b$)L$^2$(Alk)$_m$Ar;

R$^6$ is hydrogen, fluorine, or an optionally substituted alkyl group;

R$^7$ is hydrogen, fluorine, an optionally substituted straight or branched alkyl group, —OR$^c$, where R$^c$ is hydrogen or an optionally substituted alkyl or alkenyl group, or a formyl, alkoxyalkyl, alkanoyl, carboxamido or thiocarboxamido group;

each of R$^8$, R$^9$ and R$^{10}$, which may be the same or different, is hydrogen or an optionally substituted alkyl, aralkly or aryl group;

R$^{11}$ is hydrogen, fluorine or a methyl group;

X$^1$ is an oxygen or sulphur atom;

L$^1$ and L$^2$ are independently divalent linking groups;

Ar is a monocyclic or bicyclic aryl group, optionally containing one or more heteroatoms selected from oxygen, sulphur and nitrogen atoms;

Ar' is Ar, —CO(Alk)$_m$Ar, —SO$_2$(Alk)$_m$Ar, —SO$_2$NH(Alk)$_m$Ar, —SO$_2$N(Alk$^1$)(Alk)$_m$Ar, —SO$_2$N((Alk)$_m$Ar)$_2$, —CONH(Alk)$_m$Ar, —CON(Alk$^1$)(Alk)$_m$Ar, —CON((Alk)$_m$Ar)$_2$, —N(Alk$^1$)SO$_2$(Alk)$_m$Ar, —NHSO$_2$(Alk)$_m$Ar, —N(SO$_2$(Alk)$_m$Ar)$_2$, —NHSO$_2$NH(Alk)$_m$Ar, —N(Alk$^1$)SO$_2$NH(Alk)$_m$Ar, —NHSO$_2$N(Alk$^1$)(Alk)$_m$Ar, —N(Alk$^1$)SO$_2$N(Alk$^1$)(Alk)$_m$Ar, —NHSO$_2$N((Alk)$_m$Ar)$_2$, —N(Alk$^1$)SO$_2$N((Alk)$_m$Ar)$_2$, —NHC(O)(Alk)$_m$Ar, —N(Alk$^1$)C(O)(Alk)$_m$Ar, —N(C(O)(Alk)$_m$Ar)$_2$, —NHC(O)NH(Alk)$_m$Ar, —N(Alk$^1$)C(O)NH(Alk)$_m$Ar, —NHC(O)N(Alk$^1$)(Alk)$_m$Ar, —NAlk$^1$C(O)N(Alk$^1$)(Alk)$_m$Ar, —NHC(O)O(Alk)$_m$Ar, —N(Alk$^1$)C(O)O(Alk)$_m$Ar, —C(S)NH(Alk)$_m$Ar, —C(S)N(Alk$^1$)(Alk)$_m$Ar, —C(S)N(Alk$^1$)(Alk)$_m$Ar, —C(S)N((Alk)$_m$Ar)$_2$, —NHC(S)(Alk)$_m$Ar, —N(Alk$^1$)C(S)(Alk)$_m$Ar, —N(C(S)(Alk)$_m$Ar)$_2$, —NHC(S)NH(Alk)$_m$Ar, —N(Alk$^1$)C(S)NH(Alk)$_m$Ar, —NHC(S)N(Alk$^1$)(Alk)$_m$Ar, —N(Alk$^1$)C(S)N(Alk$^1$)(Alk)$_m$Ar, —SO$_2$(Alk)$_m$NHet, —CO(Alk)$_m$NHet, —CS(Alk)$_m$NHet, —NHSO$_2$(Alk)$_m$NHet, —NHC(O)(Alk)$_m$NHet, —NHC(S)(Alk)$_m$NHet, —SO$_2$NH((Alk)$_m$ Het'), —CONH((Alk)$_m$Het'), —CSNH((Alk)$_m$Het'), —NHSO$_2$NH((Alk)$_m$Het'), —NHC(O)NH(Alk)$_m$ (Het') or —NHC(S)NH(Alk)$_m$(Het');

Alk is an optionally substituted, straight or branched C$_{1-6}$alkylene, C$_{2-6}$alkenylene or C$_{2-6}$alkynylene chain optionally interrupted by one, two or three —O— or —S— atoms or —S(O)$_q$— or —N(R$^b$)— groups, where q is an integer 1 or 2;

Alk$^1$ is an optionally substituted, straight or branched C$_{1-6}$alkyl, C$_{2-6}$alkenyl or C$_{2-6}$alkynyl chain optionally interrupted by one, two or three —O— or —S— atoms or —S(O)$_q$— or —N(R$^b$)— groups;

NHet is an optionally substituted C$_{5-7}$heterocyclic amino group optionally containing one or more additional —O— or —S— atoms or —N(R$^b$)—, —CO— or —CS— groups;

Het' is an optionally substituted C$_{5-7}$monocyclic carbocyclic group optionally containing one or more —O— or —S— atoms or —N(R$^b$)— groups;

or a salt, solvate, hydrate, prodrug or N-oxide thereof; with the proviso that at least one of R$^4$ and R$^5$ is —(CH$_2$)$_t$ArN(R$^b$)CX$^1$N(R$^b$)L$^2$(Alk)$_m$Ar.

4. A compound according to claim 3 wherein L is —OR.

5. A compound according to claim 4 wherein:

R$^a$ is an optionally substituted, straight or branched C$_{1-6}$alkyl group;

R is an optionally substituted C$_{3-8}$cycloalkyl group;

R$^3$ is a hydrogen atom;

R$^4$ is —(CH$_2$)$_t$ArN(R$^b$)CX$^1$N(R$^b$)L$^3$(Alk)$_m$Ar, and

R$^5$ is —(CH$_2$)$_t$Ar.

6. A compound according to claim 5 wherein:

m and t are 0;

X$^1$ is —O—;

L$^2$ is —S(O)$_2$—;

R$^4$ is a methyl group;

R$^b$ is a hydrogen atom;

R is an optionally substituted cyclopentyl group;

R$^5$ is a pyridyl group, and

Ar is an optionally substituted phenyl group.

7. A method of preventing or treating an inflammatory disease in a patient comprising administering to the patient, in an amount effective to elevate intracellular levels of adenosine 3',5'-cyclic monophosphate (cAMP), a composition which comprises a selective inhibitor of a phosphodiesterase (PDE) IV isoenzyme selected from a compound according to claim 1 and a pharmaceutically acceptable carrier, excipient or diluent.

8. A method according to claim 7 wherein said inflammatory disease is asthma.

9. A method according to claim 7 wherein said inflammatory disease is selected from the group consisting of inflammatory airway disease, chronic bronchitis, eosinophilic granuloma, cellular proliferative disorders, endotoxic shock, septic shock, ulcerative colitis, Crohn's disease, reperfusion injuries, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis, artherosclerosis, rheumatoid arthritis, osteoarthritis, ankylosing spondylitis, transplant rejection and graft versus host disease.

10. A compound according to claim 9 wherein $R^4$ is an —Ar—N($R^b$)CXN($R^b$)$L^2$(Alk)$_m$Ar group.

11. A compound according to claim 10 wherein $L^2$ is a —S(O)$_2$— or —S(O)$_2$NH— group.

12. A compound according to claim 11 wherein $R^4$ is an —ArNHCONHS(O)$_2$Ar, —ArNHCSNHS(O)$_2$Ar, —ArNHCONHS(O)$_2$NHAr or —ArNHCSNHS(O)$_2$NHAr group where in each instance the Ar group is an optionally substituted phenyl group.

13. A compound according to claim 10 wherein L is an —XR group.

14. A compound according to claim 13 wherein Y is an —OR$^a$ group and R$^a$ is an optionally substituted alkyl group.

15. A compound according to claim 14 wherein R$^a$ is a methyl group optionally substituted by one, two or three fluorine or chlorine atoms.

16. A compound according to claim 10 wherein L is an —OR group and R is an optionally substituted cycloalkyl group.

17. A compound according to claim 16 wherein R is a cyclopentyl group.

18. A compound according to claim 10 wherein $R^3$, $R^6$ and $R^7$ is each a hydrogen atom.

19. A compound according to claim 10 wherein $R^5$ is an Ar group.

20. A compound according to claim 19 wherein $R^5$ is an optionally substituted pyridyl group.

21. A compound according to claim 20 wherein $R^5$ is an optionally substituted 4-pyridyl group.

22. A compound according to claim 6 which is N-[4-{1-(3-cyclopentyloxy-4-methoxyphenyl)-2-(4-pyridyl) ethyl}phenyl-N'-(phenylsulphonyl)urea; or a resolved enantiomer, salt, solvate, hydrate, prodrug or N-oxide thereof.

23. A compound according to claim 22 which is (R)-N-[4-{1-(3-cyclopentyloxy-4-methoxyphenyl)-2-(4-pyridyl) ethyl}phenyl-N'-(phenylsulphonyl)urea; or a salt, solvate, hydrate, prodrug or N-oxide thereof.

24. A compound which is selected from the group consisting of:

N-[4-{1-(3-cyclopentyloxy-4-methoxyphenyl)-2-(4-pyridyl)ethyl}phenyl-N'-(phenylsulphonyl) urea;

N-[4-{1-(3-cyclopentyloxy-4-methoxyphenyl)-2-(4-pyridyl)ethyl}phenyl-N'-(methylphenylsulphonyl) urea; and N-[4-{1-(3-cyclopentyloxy-4-methoxuphenyl)-2-(4-pyridyl)ethyl}phenyl-N'-(chlorophenylsulphonyl) urea: or a resolved enantiomer, salt, solvate, hydrate, prodrug or N-oxide thereof.

25. A compound according to claim 24 which is N-[4-{1-3-cylcopentyloxy-4-methoxyphenyl)-2-(4-pyridyl) ethyl}phenyl-N'-methylphenylsulphonyl) urea; or a resolved enantiomer, salt, solvate, hydrate, prodrug or N-oxide thereof.

26. A compound according to claim 25 which is (R)-N-[4-{1-3-cyclopentyloxy-4-methoxyphenyl)-2-(4-pyridyl) ethyl}phenyl-N-40 -(methylphenylsulphonyl) urea; or a salt, solvate, hydrate, prodrug or N-oxide thereof.

27. A compound according to claim 24 which is N-[4-{1-(3-cyclopentyloxy-4-methoxyphenyl)-2-(4-pyridyl) ethyl}phenyl-N'-(chlorophenylsulphonyl) urea; or a resolved enantiomer, salt, solvate, hydrate, prodrug or N-oxide thereof.

28. A compound according to claim 27 which is (R)-N-[4-{1-(3-cyclopentyloxy-4-methoxyphenyl)-2-(4-pyridyl) ethyl}phenyl-N'-(methylphenylsulphonyl) urea; or a salt, solvate, hydrate, prodrug or N-oxide thereof.

\* \* \* \* \*